United States Patent
Le Maner

(10) Patent No.: US 12,233,243 B2
(45) Date of Patent: Feb. 25, 2025

(54) DEVICE FOR DISPENSING A PULVERULENT PRODUCT

(71) Applicant: APTAR FRANCE SAS, Le Neubourg (FR)

(72) Inventor: Francois Le Maner, La Vallee Montaure (FR)

(73) Assignee: APTAR FRANCE SAS, Le Neubourg (FR)

( * ) Notice: Subject to any disclaimer, the term of this patent is extended or adjusted under 35 U.S.C. 154(b) by 238 days.

(21) Appl. No.: 17/795,173

(22) PCT Filed: Jan. 25, 2021

(86) PCT No.: PCT/FR2021/050124
§ 371 (c)(1),
(2) Date: Jul. 25, 2022

(87) PCT Pub. No.: WO2021/152246
PCT Pub. Date: Aug. 5, 2021

(65) Prior Publication Data
US 2023/0090739 A1    Mar. 23, 2023

(30) Foreign Application Priority Data
Jan. 27, 2020 (FR) .................................... 2000769

(51) Int. Cl.
*A61M 5/178* (2006.01)
*A61D 7/00* (2006.01)
(Continued)

(52) U.S. Cl.
CPC ............... *A61M 5/178* (2013.01); *A61D 7/00* (2013.01); *A61M 11/02* (2013.01);
(Continued)

(58) Field of Classification Search
CPC .... A61M 5/178; A61M 11/02; A61M 15/002; A61M 15/0028; A61M 16/04;
(Continued)

(56) References Cited

U.S. PATENT DOCUMENTS 3,788,524 A * 1/1974 Davis .................... A61J 1/2089
604/416
4,379,453 A * 4/1983 Baron ........................ B01J 7/02
604/145
(Continued)

FOREIGN PATENT DOCUMENTS

WO    2012/105236 A1    8/2012
WO    2019/054121 A1    3/2019

OTHER PUBLICATIONS

International Preliminary Report on Patentability issued Jul. 28, 2022 in International Application No. PCT/FR2021/050124.
(Continued)

*Primary Examiner* — Frederick C Nicolas
(74) *Attorney, Agent, or Firm* — Sughrue Mion, PLLC

(57) ABSTRACT

Device for dispensing a pulverulent product having a reservoir unit (100) connected on the one hand, to an air expulsion system (200) and on the other hand to a dispensing head (300) provided with a dispensing orifice (310). The reservoir unit (100) has a reservoir (110) having substantially the form of a hollow cylinder, with a distal opening (111), a proximal opening (112), and a metering passage (113) connecting the distal and proximal openings (111, 112), a one-way valve (115) being positioned between the metering passage (113) and the distal opening (111), the proximal opening (112) of the reservoir (110) forming a filling cone which tapers towards the metering passage (113) to facilitate filling of the metering passage (113) with a dose of powder.

13 Claims, 5 Drawing Sheets

(51) Int. Cl.
  *A61M 11/02* (2006.01)
  *A61M 15/00* (2006.01)
  *A61L 2/07* (2006.01)
  *A61M 16/04* (2006.01)
(52) U.S. Cl.
  CPC ............ *A61M 15/0028* (2013.01); *A61L 2/07* (2013.01); *A61M 15/002* (2014.02); *A61M 16/04* (2013.01); *A61M 2202/064* (2013.01); *A61M 2205/073* (2013.01); *A61M 2205/8281* (2013.01); *A61M 2210/1032* (2013.01); *A61M 2250/00* (2013.01)
(58) Field of Classification Search
  CPC .... A61M 2205/8281; A61M 2202/064; A61M 2205/073; A61M 2210/1032; A61M 2250/00; A61L 2/07; A61D 7/00
  See application file for complete search history.

(56) References Cited

U.S. PATENT DOCUMENTS

| | | | | |
|---|---|---|---|---|
| 5,328,099 | A * | 7/1994 | Petit | A61M 11/02 128/200.14 |
| 5,672,155 | A * | 9/1997 | Riley | B01L 3/0227 604/152 |
| 5,921,236 | A * | 7/1999 | Ohki | A61M 15/0033 128/203.15 |
| 5,989,217 | A * | 11/1999 | Ohki | A61M 15/0033 128/200.22 |
| 6,203,519 | B1 * | 3/2001 | Fagerstrom | A61M 13/00 604/27 |
| 7,278,982 | B2 * | 10/2007 | Tsutsui | A61M 15/0028 128/203.22 |
| 7,353,823 | B2 * | 4/2008 | Tsutsui | A61M 15/0028 128/203.19 |
| RE45,404 | E * | 3/2015 | Tsutsui | A61M 15/0038 128/203.18 |
| 10,071,211 | B2 * | 9/2018 | Tsutsui | A61M 16/0045 |
| 10,549,052 | B2 * | 2/2020 | Shahaf | A61M 15/0093 |
| 11,559,640 | B2 * | 1/2023 | Haruta | A61M 15/0061 |
| 2005/0177095 | A1 * | 8/2005 | Tsutsui | A61M 15/0028 604/58 |
| 2011/0045088 | A1 * | 2/2011 | Tsutsui | A61M 15/0081 424/490 |
| 2013/0338631 | A1 * | 12/2013 | Butlin | A61M 5/19 604/506 |
| 2014/0060535 | A1 * | 3/2014 | Tsutsui | A61M 11/02 128/203.15 |
| 2020/0276402 | A1 * | 9/2020 | Haruta | A61M 15/08 |

OTHER PUBLICATIONS

International Search Report for PCT/FR2021/050124 dated Jun. 9, 2021 [PCT/ISA/210].

* cited by examiner

DEVICE FOR DISPENSING A PULVERULENT PRODUCT

CROSS REFERENCE TO RELATED APPLICATIONS

This application is a National Stage of International Application No. PCT/FR20201/050124 filed Jan. 25, 2021, claiming priority based on French Patent Application No. FR2000769 filed Jan. 27, 2020.

FIELD OF THE INVENTION

The present invention relates to a device for dispensing a pulverulent product, in particular intended for the administration of pharmaceutical product in the form of powder on small animals, such as, for example, rodents, in particular mice.

BACKGROUND

The devices of the state of the art used to administer doses of powder on small animals, such as rodents, in particular mice, generally comprise a reservoir containing one single dose of powder, associated with a dispensing head on the one hand, and an air expulsion system on the other hand. During actuation, the air expulsion generates a pressurised airflow which enables to expel the dose of powder through the dispensing head, then generally through a cannula intubated in the animal to dispense the powder on its carina of trachea.

These devices generally have disadvantages. Thus, after each actuation, the empty reservoir must be replaced with a full reservoir, which is not practical for the handler, nor economical. A solution to resolve this problem is to provide a reusable reservoir, for example which could easily be filled with another dose of powder and assembled in the device before each actuation.

Another disadvantage relates to the air expulsion, generally done by a syringe containing air. With this type of air expulsion, the pressurised airflow generated during the actuation is dependent on the way in which the user actuates the device, in particular of the force with which they perform its actuation. This does not enable to perform a dispensing reproducible upon each actuation. A solution to resolve this problem is to use a pump adapted to generate a pressurised airflow, the actuation of this pump being independent of the force exerted by the user, in particular of the speed at which they perform this actuation.

Documents WO2019054121 and WO2012105236 describe devices of the state of the art comprising prefilled and single-use reservoirs.

SUMMARY OF CERTAIN ASPECTS OF THE INVENTION

The present invention aims to provide a powder dispensing device which does not reproduce the abovementioned disadvantages.

The present invention in particular aims to provide a powder dispensing device which enables to dispense several doses in several successive actuations.

The present invention also aims to provide a powder dispensing device which enables to easily fill the reservoir with a dose of powder before each actuation.

The present invention also aims to provide a powder dispensing device which is simple and reliable to use, with a dispensing reproducible upon each actuation.

The present invention also aims to provide a powder dispensing device which is simple and inexpensive to manufacture and to assemble.

The present invention thus provides a device for dispensing a pulverulent product comprising a reservoir unit connected on the one hand, to an air expulsion system and on the other hand to a dispensing head provided with a dispensing orifice, said reservoir unit comprising a reservoir having substantially the form of a hollow cylinder, with an opening that is distal relative to said dispensing orifice, an opening that is proximal relative to said dispensing orifice, and a metering passage connecting said distal and proximal openings, a one-way valve being positioned between said metering passage and said distal opening, said proximal opening of said reservoir forming a filling cone which tapers towards said metering passage to facilitate filling of said metering passage with a dose of powder.

Advantageously, said reservoir is fixed in a cylindrical body comprising a central passage enabling to connect said air expulsion system with said reservoir.

Advantageously, the reservoir is fixed in said cylindrical body with interposition of a seal.

Advantageously, said cylindrical body is made of metal, in particular, made of stainless steel.

Advantageously, said reservoir is made of metal, in particular, made of stainless steel.

Advantageously, said one-way valve is of the split membrane type which only opens in one single direction under the effect of a predetermined pressure.

Advantageously, said air expulsion system comprises an air pump.

Advantageously, said dispensing head comprises a dispensing member provided with said dispensing orifice.

Advantageously, said dispensing member is a needle.

Advantageously, said needle is curved or bent.

BRIEF DESCRIPTION OF THE DRAWINGS

These characteristics and advantages and others of the present invention appear more clearly from the following detailed description, given by way of non-limiting example, and with reference to the accompanying drawings, and in which.

DETAILED DESCRIPTION OF NON-LIMITING EMBODIMENTS OF THE INVENTION

The terms "proximal" and "distal" are relative to the dispensing orifice. The terms "upstream" and "downstream"

refer to the flow direction of the fluid product during its dispensing. The terms "axial" and "radial" are relative to the longitudinal central axis of the device.

The fluid product dispensing device represented in the Figures comprises a reservoir unit 100 which could contain a dose of pulverulent product, connected on the one side to an air expulsion system 200 and on the other side to a dispensing head 300 provided with a dispensing orifice 310.

The reservoir unit 100, more particularly visible in FIGS. 12 and 13, comprises a reservoir 110 having substantially the form of a hollow cylinder, with a distal opening 111, a proximal opening 112 and a metering passage 113 connecting said two distal and proximal openings 111, 112. A one-way valve 115 is arranged between said metering passage 113 and said distal opening 111.

The reservoir 110 is intended to be filled with a dose of powder before each use of the device. This filling is generally done manually by the user from a powder storage container, through the proximal opening 112. The reservoir 110 is thus reusable.

Thus, when the reservoir 110 is filled with a dose of powder through the proximal opening 112, this dose of powder remains in the metering passage 113, the one-way valve 115 preventing it from exiting through the distal opening 111. When the air expulsion system 200 is actuated, a pressurised airflow is sent into the reservoir 110 through said distal opening 111, causing the opening of the one-way valve 115 and the expulsion of the dose of powder through the proximal opening 112.

The reservoir 110 is preferably fixed in a cylindrical body 105 comprising a central passage 106 enabling to connect the air expulsion system 200 with the reservoir 110.

As visible in FIG. 13, the proximal opening 112 of the reservoir 110 forms a filling cone which tapers towards said metering passage 113 to facilitate the filling of the metering passage 113 with the dose of powder. Indeed, the doses intended for small animals, such as rodents, are generally very small, typically of around a few $mm^3$. Advantageously, it is the volume of the metering passage 113 which defines the volume of the dose of powder dispensed upon each actuation. This elongated tubular shape extended of the metering passage 113 enables in particular to limit the risks of agglomeration of the powder.

The reservoir 110 is advantageously fixed in the cylindrical body 105 with interposition of a seal 107.

The one-way valve 115 can be of the split membrane type which only opens in one single direction under the effect of a predetermined pressure. Other implementations, for example a ball, are possible.

Such a reservoir unit 100 in particular enables to easily perform a sterilisation in an autoclave.

Advantageously, the reservoir 110 is made of metal, in particular, made of stainless steel. This enables to avoid the use of plastic materials in the expulsion path of the powder. The cylindrical body 105 can also be made of metal, in particular made of stainless steel. In this way, the reservoir unit 100 can easily be connected to the ground to avoid or limit static electricity phenomena.

The dispensing head 300 comprises a hollow body 301 fixed to the reservoir unit 100 by a fixing ring 302.

The fixing ring 302 is fixed on the cylindrical body 105 of the reservoir unit 100, for example by screwing, snap-fitting or crimping. Any other fixing means is possible.

The hollow body 301 comprises a central axial passage 303, connected on a side to the proximal opening 112 of the reservoir 110 and on the other side to a dispensing member 311 provided with a dispensing orifice 310. In the example represented, the dispensing member 311 is a needle, which can be curved or bent. In a variant, a dispensing member enabling to deliver an aerosol could be considered.

Advantageously, a hollow stopper 305 is interposed between the reservoir 110 and the hollow body 301, said hollow stopper 305 having a conical shape adapted to the shape of the proximal opening 112 of the reservoir 110. This hollow stopper 305 enables to ensure a good connection between the reservoir 110 and the hollow body 301, in particular a sufficient sealing to avoid any loss of dose during the dispensing of a dose of powder.

The air expulsion system 200 can be, in a known manner, an air-filled syringe, the actuation of the piston generating a pressurised airflow.

Preferably, however, the air expulsion system 200 comprises a pump, of which the actuation is independent of the actuation force exerted by the user. Thus, the pressurised airflow generated upon each actuation is always identical and reproducible from one actuation to the other.

An advantageous example of the air expulsion system 200 will now be described in more detail in reference to FIGS. 1 to 11.

In this example, the air expulsion is formed by a pump 200 comprising an external body 210 provided with a handle 211 and a dispensing nozzle 215. The external body 210 contains a pump body comprising a pumping chamber 225, and in which there is arranged a rod 230 acting as a piston. The rod 230 is fixed with respect to the external body 210, and the pump body is axially movable to slide around said rod 230 between a rest position and an actuation position.

The pump body comprises a proximal hollow body 220 and a distal hollow body 270, which are fixed to one another, in particular by screwing. A body seal 260 is provided between the proximal and distal hollow bodies to ensure a sealing fixing to one another. The proximal hollow body 220 comprises a proximal pump body part 221 and a distal pump body part 222 of which the inside diameter is greater than that of said proximal pump body part 221. The distal hollow body 270 extends at least partially in the proximal hollow body 220.

Said rod 230 comprises a proximal rod part 231, a central rod part 232 and a distal rod part 233. The outside diameter of said central rod part 232 is greater than the diameters of the proximal 231 and distal 233 rod parts. The central rod part 232 supports a first seal 237 and a second seal 236, and the distal rod part 233 supports a third seal 235. The proximal rod part 231 comprises a central passage 234 which extends from the dispensing nozzle 215 into the central rod part 232 beyond said first seal 237 and which opens laterally to the outside of said central rod part 232 between said first and second seals 237, 236. The distal rod part 233 slides in said distal hollow body 270, said third seal 235 performing the sealing therebetween during actuation.

The distal hollow body 270 contains at least one spring 240, 241 collaborating on the one hand with the distal rod part 233 and on the other hand with the distal hollow body 270. In the example represented in the drawings, there are two springs 240, 241 arranged axially behind one another by being connected by a connecting member 245. Naturally, one single spring can be considered.

Possibly, an adjustment element 250, such as an adjustment screw, can be arranged in the distal hollow body 270 to form the contact with the spring 240. This adjustment element 250 thus enables to easily modify the actuation force exerted by the spring(s) on the rod 230 during the actuation.

FIGS. 5 to 10 illustrate an advantageous actuation cycle of this air pump.

Figure 1:
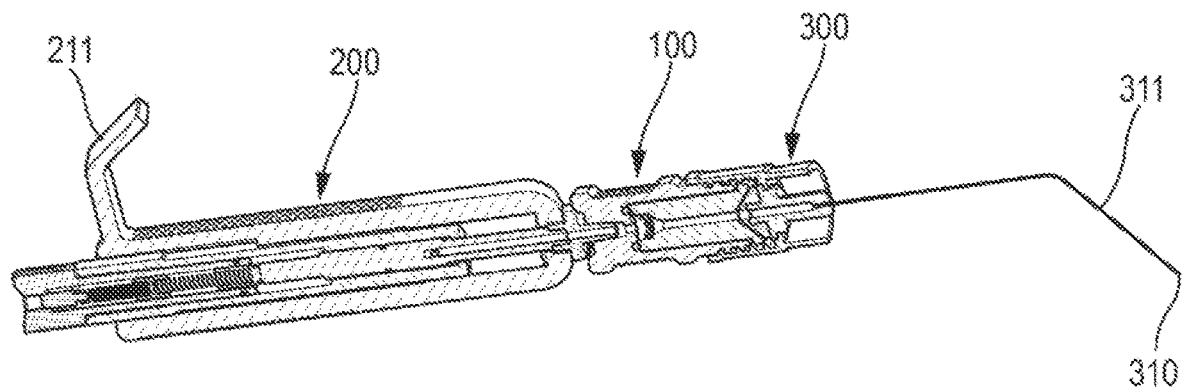
FIG. 1 is a cross-sectional, perspective, schematic view of a powder dispensing device according to an advantageous embodiment, in position before actuation.
Figure 2:
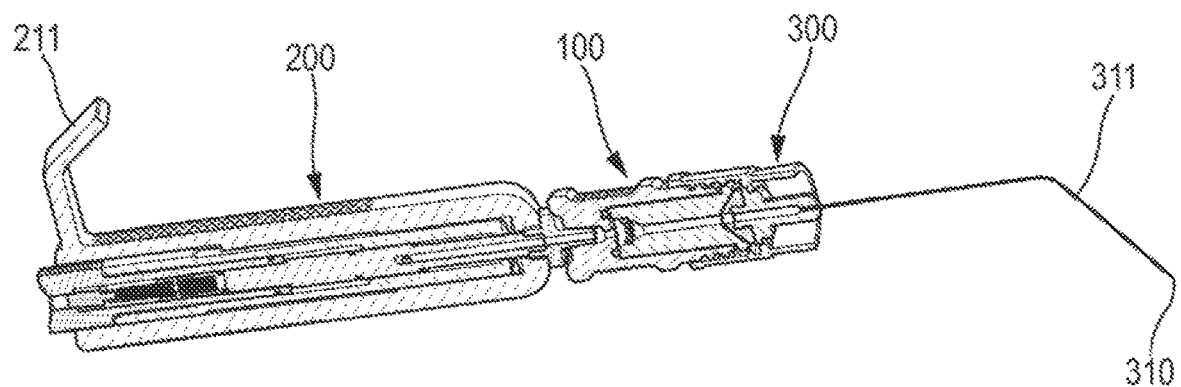
FIG. 2 is a view similar to the view in FIG. 1, shown after actuation.
Figure 3:
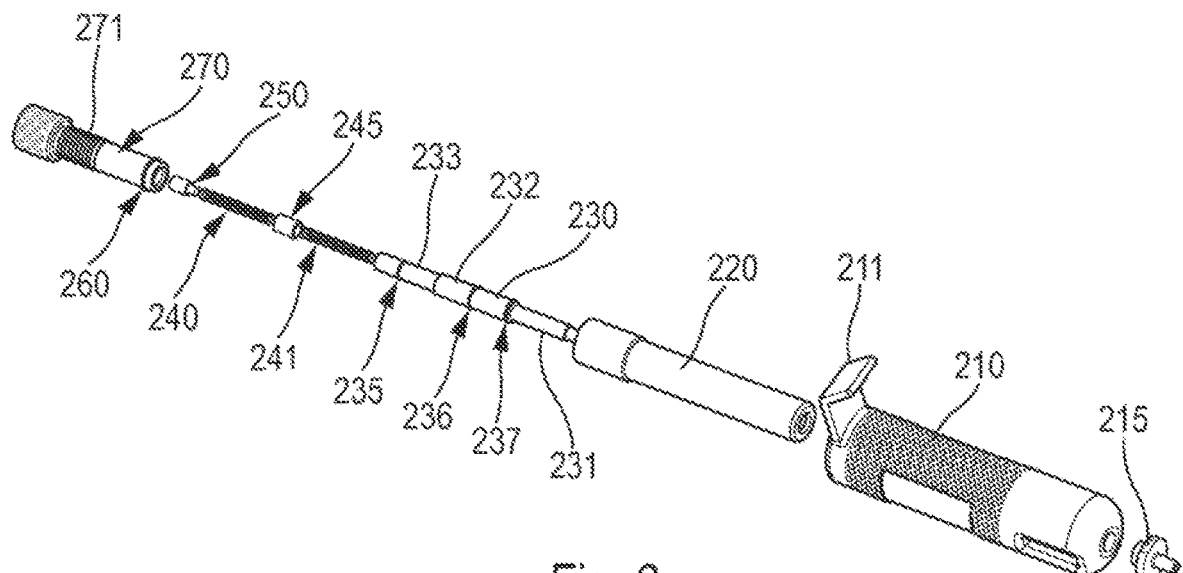
FIG. 3 is an exploded, perspective view of an air expulsion system according to an advantageous embodiment.
Figure 4:
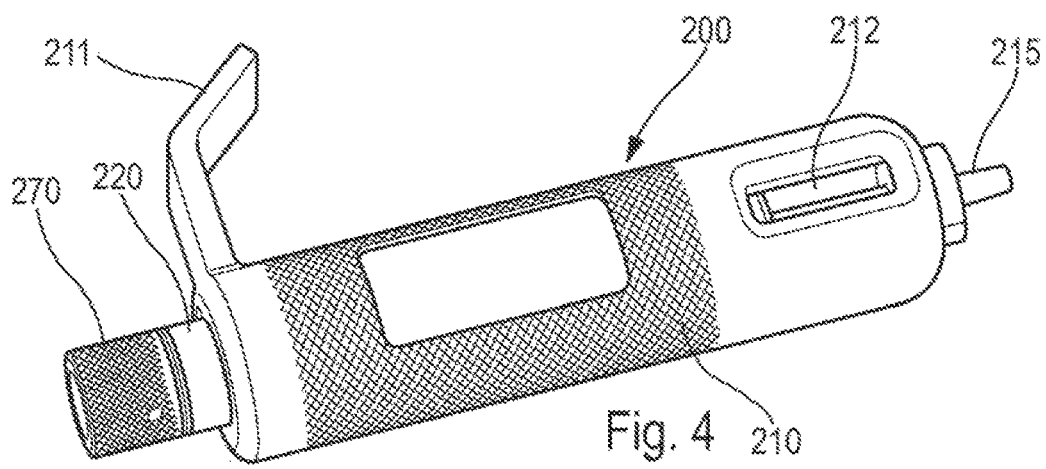
FIG. 4 is a side, perspective view of the air expulsion system of FIG. 3, FIGS. 5 to 10 are cross-sectional, perspective views of the air expulsion system of FIG. 3, showing the different steps of an actuation cycle of said air expulsion system.
Figure 5:
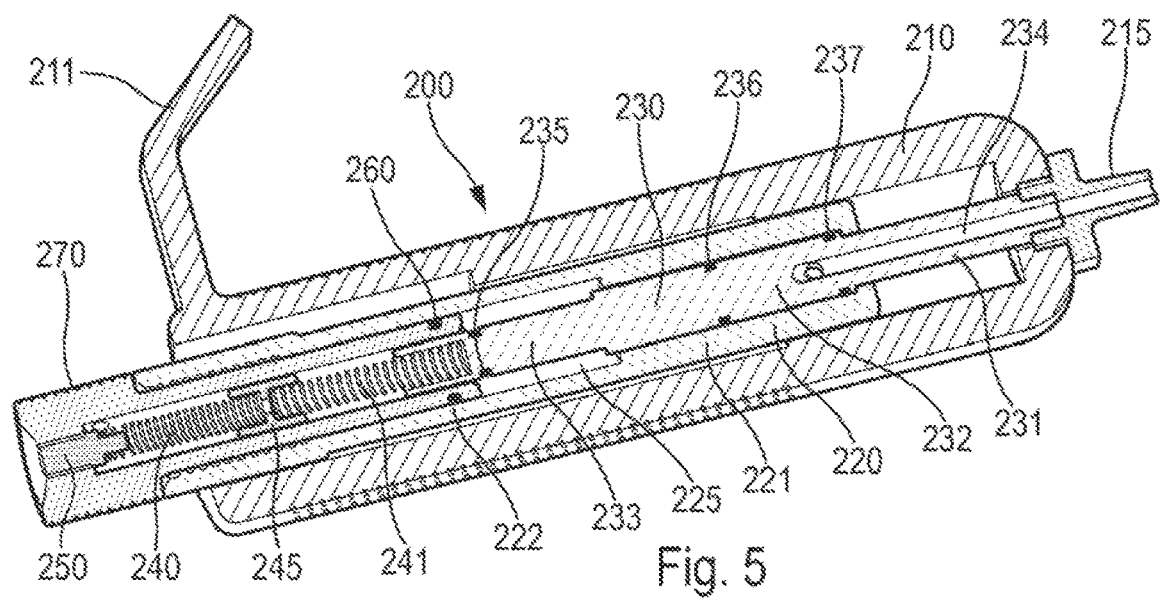

In the rest position, represented in FIG. 5, the pump body is urged axially towards the outside of the external body 210 by the springs 240, 241, the first and second seal 237, 236 collaborate in a sealed manner with the proximal pump body part 221 of the proximal hollow body 220. The dosing chamber 225 is therefore isolated from the dispensing nozzle. The third seal 235 is arranged outside of the distal hollow body 270, such that the dosing chamber 225 is open to the atmosphere via the distal hollow body 270.

Figure 6:
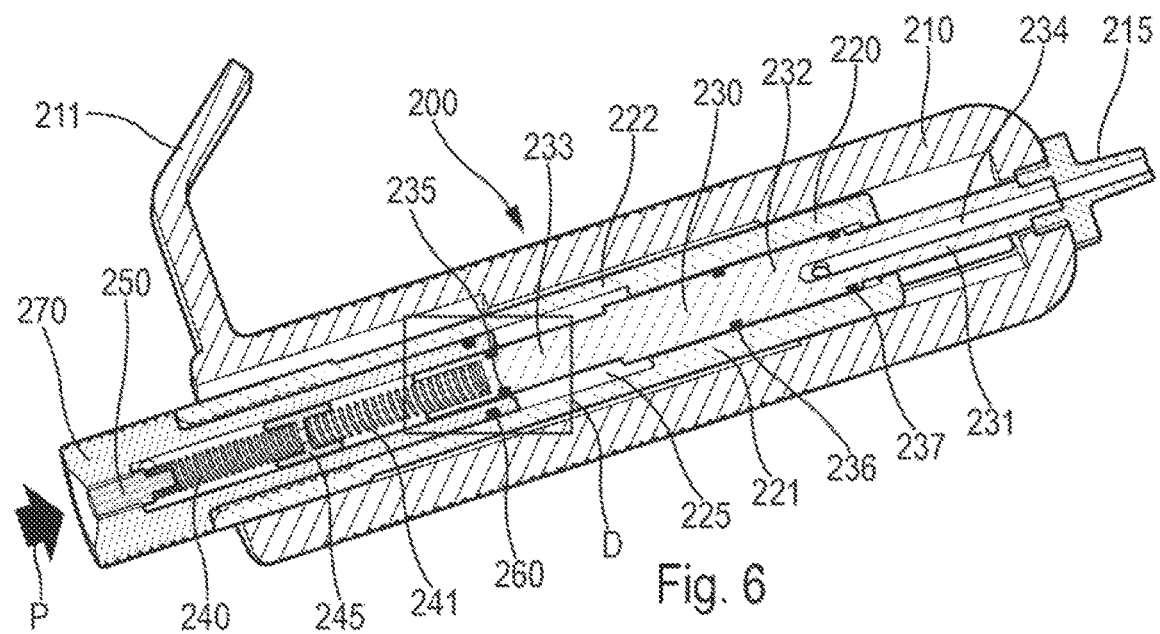
Figure 11:
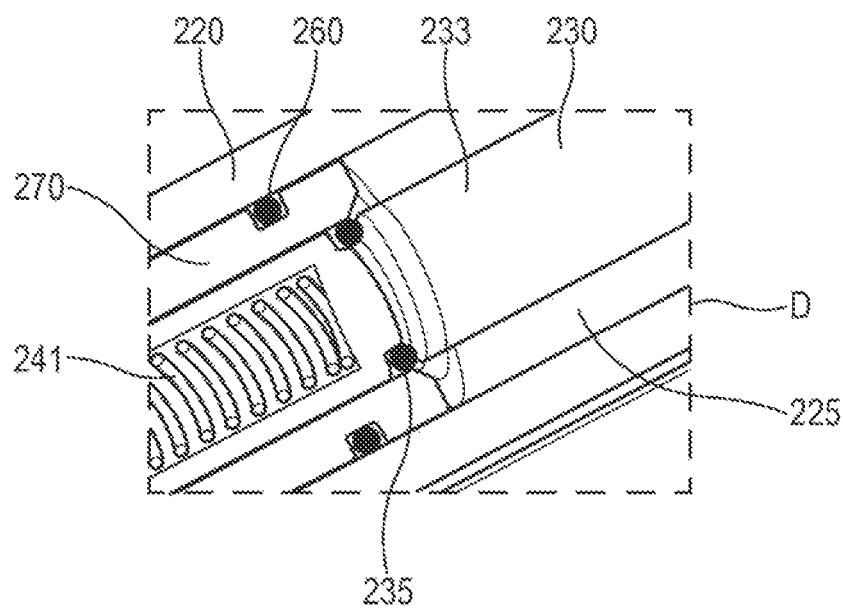
FIG. 11 is a larger-scale view of a detail D of FIG. 6.
Figure 12:
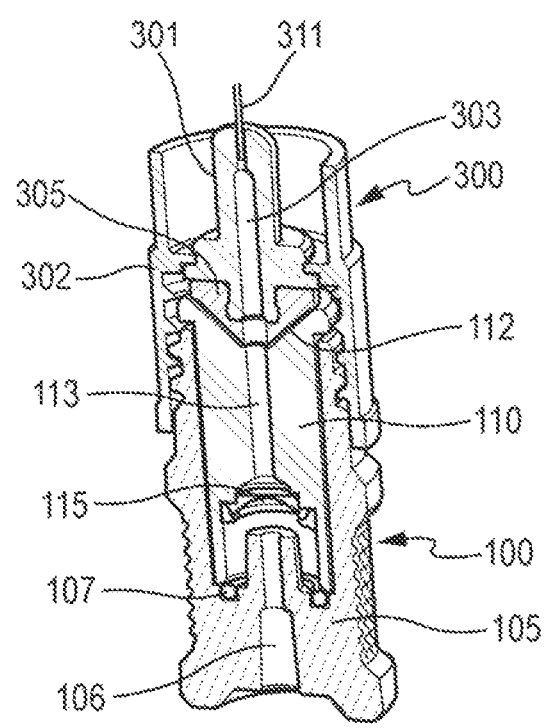
FIG. 12 is a cross-sectional, perspective view of a reservoir and dispensing head assembly, according to an advantageous embodiment.
Figure 13:
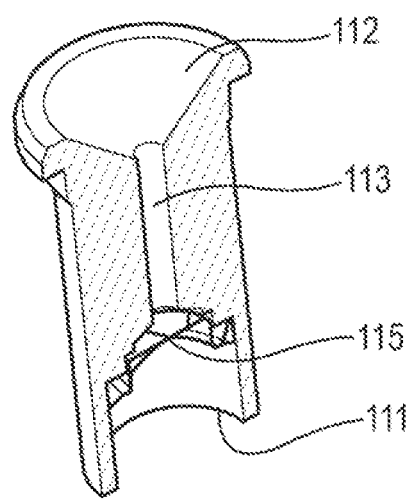
FIG. 13 is a detailed view of the reservoir of FIG. 12.

When the user exerts an axial thrust force on the distal hollow body 270, as illustrated by the arrow P in FIG. 6, the pump body, formed by the proximal hollow body 220 and the distal hollow body 270, slides axially towards the inside of the external body 210, around the rod 230. As can be better seen in FIG. 11, the third seal 235 thus collaborates in a sealed manner with the internal surface of the distal hollow body 270, to thus isolate the dosing chamber 225 from the atmosphere.

Figure 7:
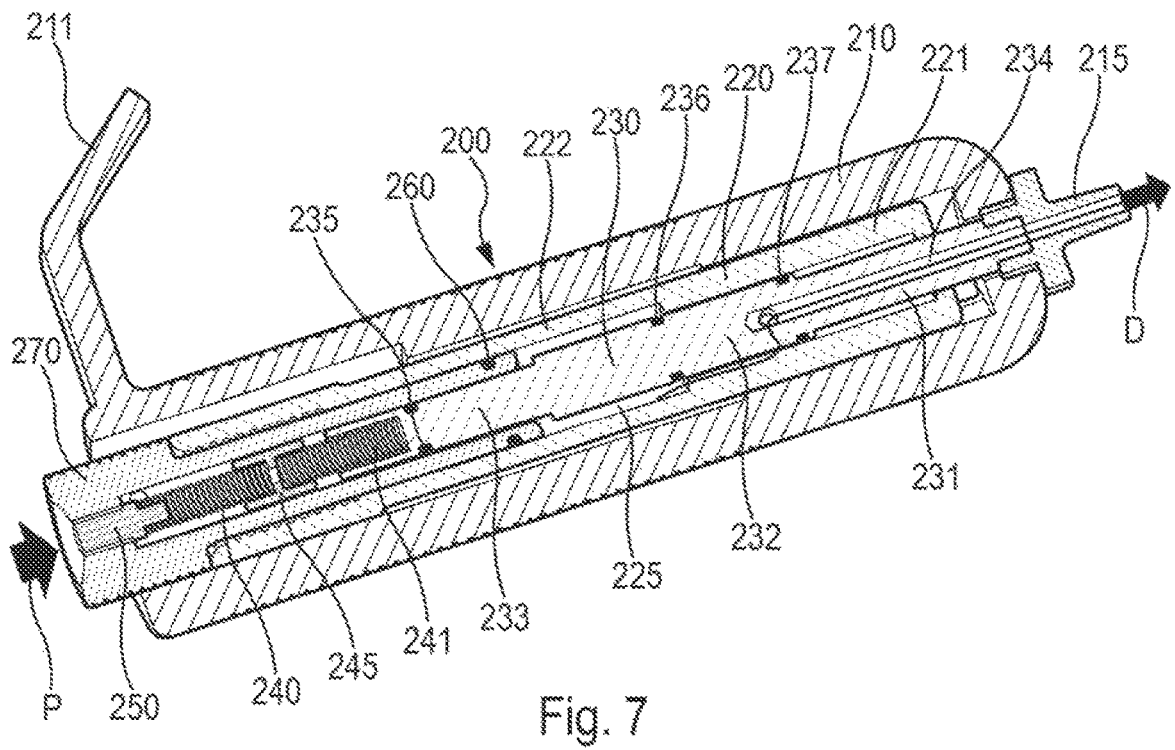

A continuation of the axial thrust force P such as illustrated in FIG. 7 thus causes the compression of air in the dosing chamber 225, under the effect of the central rod part 232 of a larger diameter which progressively penetrates into the dosing chamber 225. When the seal seal 236 reaches the distal pump body part 222 of a greater diameter and ceases to collaborate in a sealed manner with the proximal pump body part 221, the compressed air contained in the dosing chamber 225 can escape around the central rod part 232 to the central passage 234 then to the dispensing nozzle 215, as illustrated by the arrow D in FIG. 7.

Figure 8:
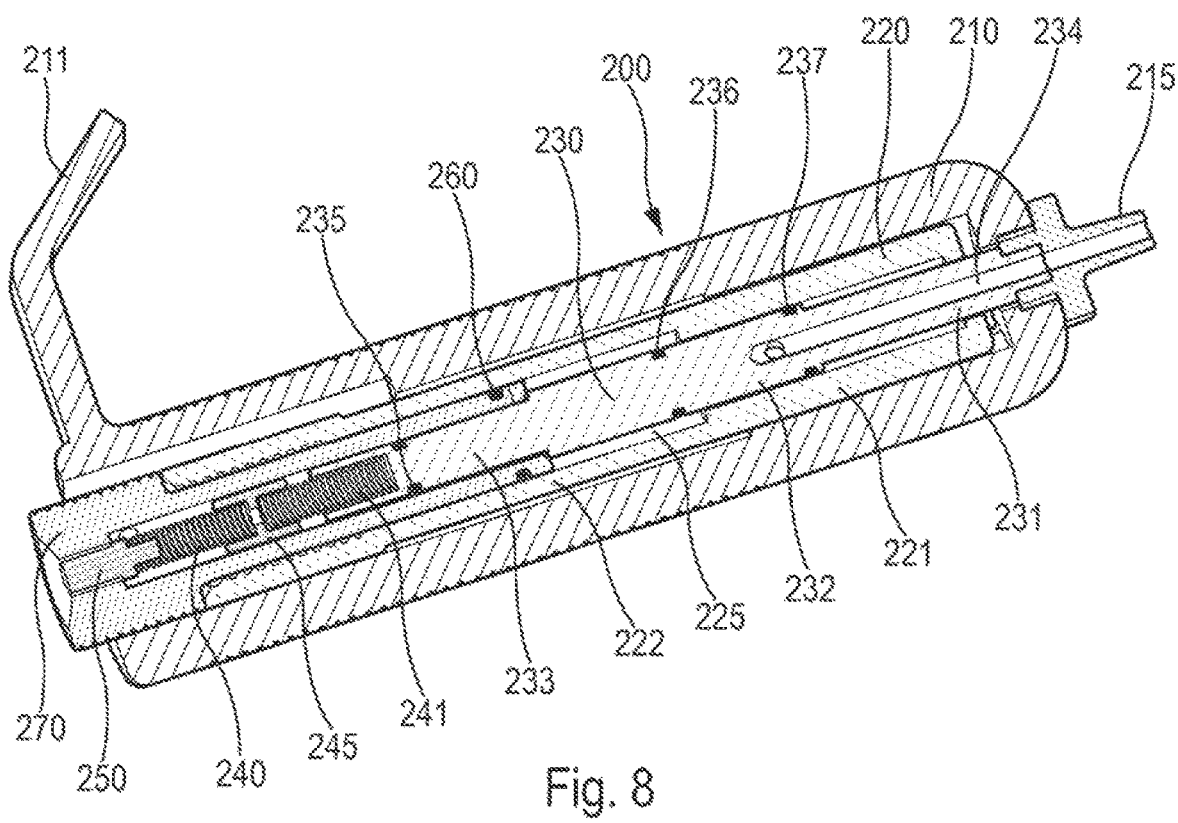

FIG. 8 shows the position at the end of the actuation stroke, after expulsion of the compressed air contained in the dosing chamber 225. In this position, the proximal axial end of the distal hollow body 270 abuts against the shoulder formed between the distal rod part 233 and the central rod part 232. This mechanical abutment of the actuation stroke of the pump ensures an actuation independent of the force exerted by the user.

Figure 9:
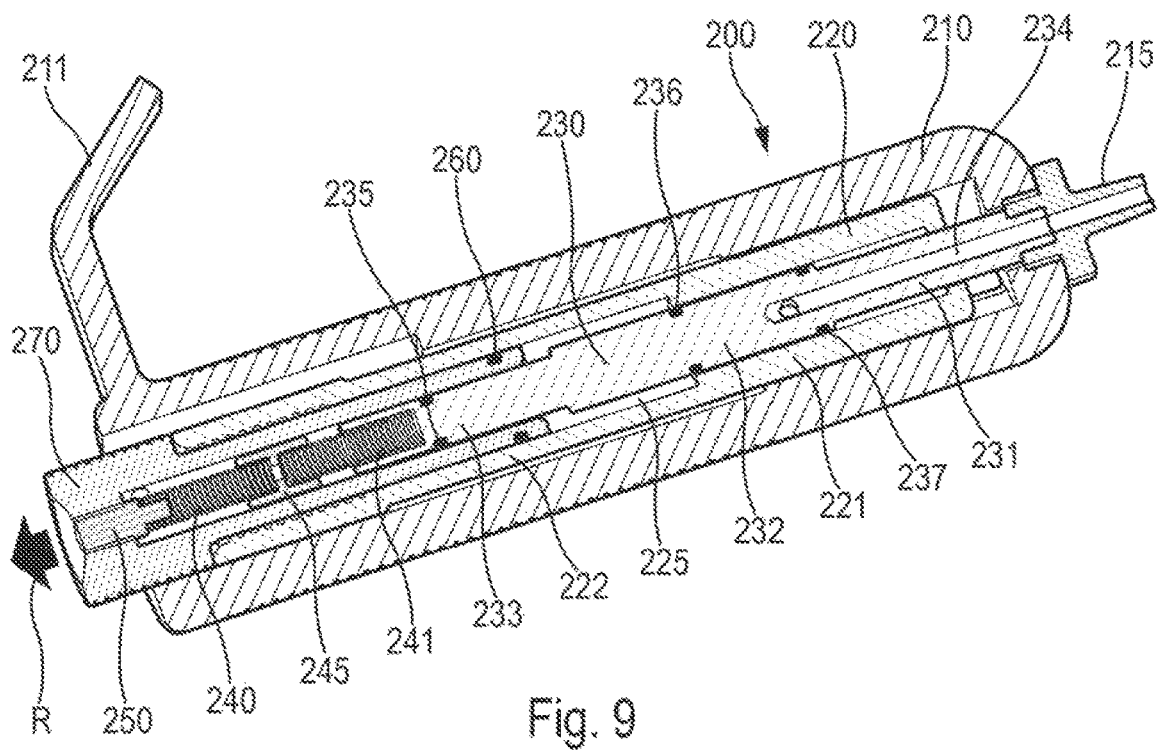

When the user relaxes their pressure on the pump body, the spring 240, 241 which has been compressed during the actuation stroke, expands, which returns the pump body to its rest position, as illustrated by the arrow R in FIG. 9. As soon as the second seal 236 again collaborates in a sealed manner with the central rod part 232, the dosing chamber 225 is again isolated from the dispensing nozzle 215, such that there is no other risk of re-suctioning of fluid product or air from the treated animal, despite the depression which is created in the dosing chamber 225 during the return stroke.

Figure 10:
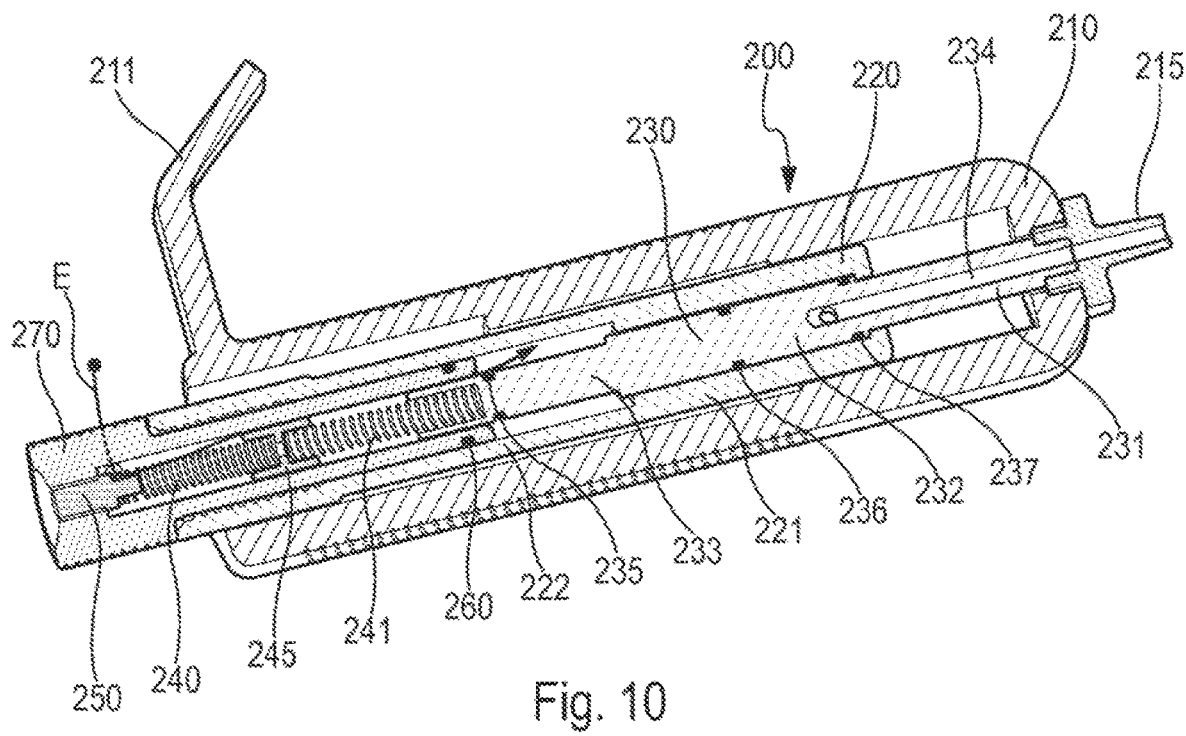

As soon as the third seal 235 ceases its sealed collaboration with the internal surface of the distal hollow body 270, the dosing chamber 225 again opens towards the atmosphere generating a venting flow through the distal hollow body 270, represented by the arrow E in FIG. 10.

The pump is thus ready for another use.

Although the present invention is described above with reference to an advantageous embodiment, naturally various modifications can be applied thereto by the person skilled in the art, without going beyond the ambit of the present invention, as defined by the accompanying claims.

The invention claimed is:

1. A device for dispensing a pulverulent product comprising a reservoir unit connected to an air expulsion system and to a dispensing head provided with a dispensing orifice, wherein said reservoir unit comprises a reservoir with an opening that is distal relative to said dispensing orifice, an opening that is proximal relative to said dispensing orifice, and a metering passage connecting said distal and proximal openings, a one-way valve being positioned between said metering passage and said distal opening, said proximal opening of said reservoir forming a filling cone which tapers towards said metering passage to facilitate filling of said metering passage with a dose of powder.

2. The device according claim 1, wherein said reservoir is fixed in a cylindrical body comprising a central passage enabling to connect said expulsion system with said reservoir.

3. The device according to claim 2, wherein said reservoir is fixed in said cylindrical body with interposition of a seal.

4. The device according to claim 2, wherein said cylindrical body is made of metal.

5. The device according to claim 1, wherein said reservoir is made of metal.

6. The device according to claim 1, wherein said one-way valve is a split membrane that only opens in one single direction under an effect of a predetermined pressure.

7. The device according to claim 1, wherein said air expulsion system comprises an air pump.

8. The device according to claim 1, wherein said dispensing head comprises a dispensing member provided with said dispensing orifice.

9. The device according to claim 8, wherein said dispensing member is a needle.

10. The device according to claim 9, wherein said needle is curved or bent.

11. The Device according to claim 1, wherein said reservoir is in the form of a hollow cylinder.

12. The device according to claim 4, wherein said metal is stainless steel.

13. The device according to claim 5, wherein said metal is stainless steel.

* * * * *